US006190888B1

(12) United States Patent
Hoshino et al.

(10) Patent No.: US 6,190,888 B1
(45) Date of Patent: Feb. 20, 2001

(54) PROCESS FOR MAKING RIBOFLAVIN GLUCOSIDE

(75) Inventors: Tatsuo Hoshino, Kamakura; Setsuko Masuda, Yokohama, both of (JP)

(73) Assignee: Roche Vitamins Inc., Parsippany, NJ (US)

( * ) Notice: Under 35 U.S.C. 154(b), the term of this patent shall be extended for 0 days.

(21) Appl. No.: 09/204,186

(22) Filed: Dec. 3, 1998

(30) Foreign Application Priority Data

Dec. 4, 1997 (EP) ................................................. 97121315

(51) Int. Cl.$^7$ ............................................. C12P 19/28
(52) U.S. Cl. ...................... 435/85; 435/252.5; 536/17.3; 544/251
(58) Field of Search .................. 544/251; 435/85, 435/252.5; 536/17.3

(56) References Cited

U.S. PATENT DOCUMENTS

| 3,669,835 | 6/1972 | Suzuki . |
| 5,837,528 | 11/1998 | Perkins et al. . |

FOREIGN PATENT DOCUMENTS

| 405 370 | 1/1991 | (EP) . |
| 821 063 | 1/1998 | (EP) . |
| 7-203982 | 8/1995 | (JP) . |

OTHER PUBLICATIONS

Balows et al., ed., "The Prokaryotes" vol. II, 1992, p. 1762.*
Yamasaki, et al., "Purification and Properties of α–Glucosidase from *Penicillium purpurogenum*," *Agricultural and Biological Chemistry*, 40(4), 669–676 (1976).

Kometani, et al., "Purification and Characterization of Cyclodextrin Glucanotransferase from an Alkalophilic Bacillus Species and Transglycosylation at Alkaline pHs," *Biosci. Biotechnol. Biochem.*, 58(3), 517–20 (1994).

Kitahata, et al., "Comparison of Action of Cyclodextrin Glucanotransferase from *Bacillus megaterium, B. circulans, B. stearothermophilus* and *B. macerans*," *J. Jap. Soc. Starch Sci.*, vol. 29, No. 1, pp. 13–18 (1982).

Tanaka, et al., "Characterization of *Bacillus stearothermophilus* cyclodextrin glucanotransferase in ascorbic acid 2–O–α–glucoside formation," *Biochimica et Biophysica Acta*, 1078(2), pp. 127–132 (1991).

Whitby, Methods in Enzymology, Academic Press, 18B, 404–417 (1971).

Whitby, J. Biochem. 50, 433–438 (1952).

Katagiri et al., J. Vitaminology 6, 139–144 (1960).

* cited by examiner

Primary Examiner—Irene Marx
(74) Attorney, Agent, or Firm—Mark E. Waddell; Stephen M. Haracz; Bryan Cave LLP

(57) ABSTRACT

A process for producing riboflavin glucoside comprises cultivating a microorganism belonging to the genus Bacillus, such as *Bacillus brevis, Bacillus cereus, Bacillus circulans, Bacillus coagulans, Bacillus licheniformis, Bacillus megaterium, Bacillus pumilus* or *Bacillus subtilis*, which is capable of producing riboflavin glucosides, in an aqueous medium containing a starch under aerobic conditions. Amongst the preferred strains are *Bacillus subtilis* RB50::[pRF69]60Ade+ and *Bacillus subtilis* RB50::[pRF69]60 [pRF93]120Ade+. The so-produced riboflavin glucoside can be used as a more soluble substitute for riboflavin to prepare clear drinks and injection solutions.

14 Claims, 1 Drawing Sheet

PROCESS FOR MAKING RIBOFLAVIN GLUCOSIDE

FIELD OF THE INVENTION

This invention relates to a process for producing riboflavin glucoside from starch by fermentation. The term "riboflavin glucoside" as used in this specification embraces riboflavin glucosides featuring one or more glucose moieties per molecule of riboflavin.

BACKGROUND OF THE INVENTION

Riboflavin glucoside is known as one of the metabolites of riboflavin found in urine. It is more soluble in water than riboflavin. The solubility of riboflavin glucoside at 20° C. and 37° C. is 2.2 and 3.5 mg/ml, respectively. In comparison, riboflavin has a solubility of 0.1 and 0.2 mg/ml at these temperatures [see Methods in Enzymology, Academic Press, 18B, 404–417 (1971)].

Riboflavin itself is widely used as an additive in drinks for colouring and/or nutrition, but the drinks become cloudy because of its low solubility in water. Riboflavin-containing solutions for intravenous drop injection also become turbid and tend to block the injection tubes. To solve such solubility problems the more soluble riboflavin glucoside could be used instead of riboflavin to prepare clear drinks and injection solutions.

Riboflavin glucoside was first obtained by Whitby with the acetone-dried powder of rat liver [Biochem. J. 50, 433 (1952)]. Glucosidation of riboflavin occurs when riboflavin is incubated in a solution containing transglucosidase and glucosyl donors such as maltose, dextrin, starch, glycogen and salicin. Transglucosidase has been reported to be widely distributed in animal organs, microorganisms and plants such as rat liver, *Aspergillus oryzae, Escherichia coli, Leuconostoc mesenteroides*, and cotylendons of pumpkin, *Cucurbita pepo*, and of sugar beet, *Beta vulgaris*. However, the productivity of riboflavin glucoside by these enzymatic reaction methods or fermentation in media containing riboflavin and glucosyl donors has been rather low, and its purification procedure too complicated, for practical use [see J. Vitaminology 6, 139–144 (1960) and Methods in Enzymology 18B, 404–417 (1971)].

SUMMARY OF THE INVENTION

By means of the process of the present invention, it is possible to produce riboflavin glucoside in a much higher yield, even without the addition of riboflavin, by the fermentation of a riboflavin glucoside-producing microorganism in a medium containing a starch. Said process comprises cultivating a microorganism belonging to the genus Bacillus which is capable of producing riboflavin glucosides in an aqueous medium containing a starch under aerobic conditions.

DETAILED DESCRIPTION OF THE INVENTION

Figure 1:
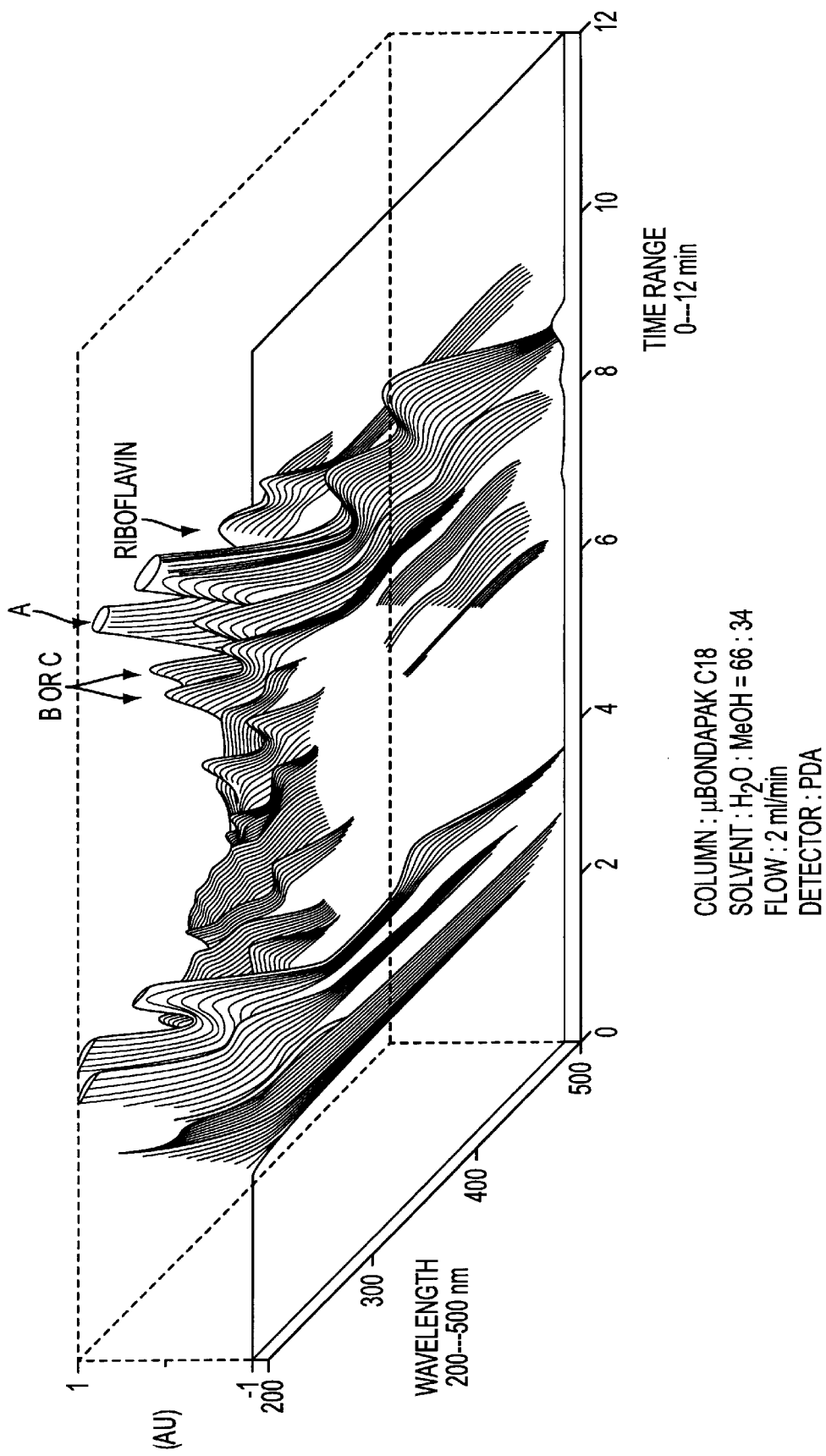
FIG. 1 shows an HPLC analysis of a typical culture broth in accordance with the present invention.

By means of the process of the present invention, it is possible to produce riboflavin glucoside in a much higher yield, even without the addition of riboflavin, by the fermentation of a riboflavin glucoside-producing microorganism in a medium containing a starch. Said process comprises cultivating a microorganism belonging to the genus Bacillus which is capable of producing riboflavin glucosides in an aqueous medium containing a starch under aerobic conditions.

The microorganisms which may be used in the present invention include all strains belonging to the genus Bacillus possessing amylase activity, e.g. those strains selected from the group *Bacillus brevis, Bacillus cereus, Bacillus circulans, Bacillus coagulates, Bacillus licheniformis, Bacillus megaterium, Bacillus pumilus* and *Bacillus subtilis*, and its recombinants which are capable of producing riboflavin.

Some of these microorganism strains are deposited at the Institute for Fermentation, Osaka, Japan (IFO). These have the accession designations *Bacillus brevis* IFO 15304, *Bacillus cereus* IFO 15305, *Bacillus circulars* IFO 13626, *Bacillus coagulans* IFO 12583, *Bacillus licheniformis* IFO 12200, *Bacillus megaterium* IFO 15308, *Bacillus pumilus* IFO 12092 and *Bacillus subtilis* IFO 13719, and are listed in the IFO's "List of Cultures", Microorganisms, 10th Edition 1996. As such, samples of the microorganisms are publicly available from the IFO.

Examples of the strains most preferably used in the present invention are *Bacillus subtilis* RB50::[pRF69]60:: [pRF93]120Ade+, *Bacillus subtilis* RB50::[pRF69]60Ade+ and the like [European Patent Publications (EP) 405370 A1 and 821063 A2. EP 405370 corresponds to U.S. patent application Ser. No. 08/384,626, filed Feb. 6, 1995, which is a continuation application of Ser. No. 07/873,572, filed Apr. 21, 1992, now abandoned, which is a continuation application of Ser. No. 07/581,048, filed Sep. 11, 1990, now abandoned, which is a continuation-in-part application of Ser. No. 07/370,378, filed Jun. 22, 1989. EP 821063 corresponds to U.S. patent application Ser. No. 08/899,241, filed Jul. 23, 1997. The contents of the aforementioned United States patent applications are hereby incorporated by reference.] The host strain, RB50, is a deregulated *Bacillus subtilis* strain resistant to roseoflavin. A plasmid pRF69 contains the SPO1-15 promoter and cat gene in the same direction as the rib operon. The details of the host microorganism and a plasmid pRF69 are given in EP 405370 A1. Said host microorganism RB50 and plasmid pRF69 have been deposited under the Budapest Treaty at the Agricultural Research Culture Collection (NRRL), Peoria, Ill., and the American Type Culture Collection (ATCC), Rockville, Md., respectively, under the following deposit nos. on the given dates:

Bacillus subtilis RB50: (NRRL) B-18502 (originally May 23, 1989; redeposited Aug. 24, 1989)

| pRF69: | ATCC 68338 | (June 6, 1990) |

The former deposit was made by S. L. Misrock, c/o Pennie & Edmonds, 1155 Avenue of the Americas, New York, N.Y. 10036, USA. As a result of various changes of responsibility for this deposit the current depositor is effectively Hoffmann-La Roche Inc., 340 Kingsland Street, Nutley, N.J. 07110. The latter deposit was made by Bio-Technica International, Inc., 85 Bolton Street, Cambridge, Mass. 02140, USA (the current depositor in this case is OmniGene Bioproducts, Inc., 763-D Concord Avenue, Cambridge, Mass. 02138).

RB50:: [pRF69]60Ade+ is prepared by introducing pRF69 to the rib site of RB50 following by the gene amplification by selecting for colonies that grow in the presence of increasing level of chloramphenicol. A plasmid pRF93 is derived from pRF89 (see FIG. 14 of EP 405370 A1) by exchanging chloramphenicol-resistant gene for tetracycline-resistant gene (see Example 8, Second site Integration, of EP 405370 A1). RB50::[pRF69]60::[pRF93]120Ade+ is obtained by integrating the second plasmid, pRF93, at bpr site of the chromosome (EP 821063 A2). The recombinant strains possessing modified rib operon at the sites of chromosome are amplified by drug resistance.

*Bacillus subtilis* RB50::[pRF69]60::[pRF93]120Ade+ is known to be capable of producing more than 14.0 g/l of riboflavin under the optimized jar fermentation condition (EP 821063 A2). The preparation of a plasmid pRF93 is also described in the said European patent publication.

In a preferred embodiment of the present invention, the production of riboflavin glucosides is effected by cultivating the last-mentioned microorganism strain in an aqueous culture medium containing a starch, especially a soluble starch and/or one or more other starches and supplemented with appropriate nutrients under aerobic condition. Said medium contains a soluble starch and/or one or more other starches at a total concentration from about 25 g/l to about 400 g/l, preferably from about 200 g/l to about 300 g/l. The amount of inoculum of microorganism is generally about 1% to about 30%, preferably about 5% to about 20%.

The culture medium contains starch, of which in principle any sort can be used, such as soluble starch, potato starch, corn starch and wheat starch. It is usually required that the culture medium also contains nutrients. These may be digestible nitrogen sources, such as organic substances, for example, peptone, yeast extract, soybean meal, corn steep liquor, cottonseed refuse, dried yeast and meat extract; inorganic substances, for example, ammonium sulfate, ammonium chloride, ammonium phosphate, potassium nitrate and potassium phosphate; vitamins; metals; amino acids; trace elements; and additional assimilable carbon sources, for example D-glucose, D-fructose, D-mannose, D-sorbitol, D-mannitol, sucrose, molasses, starch hydrolyzates, acetic acid and ethanol if necessary.

The cultivation is conveniently conducted at a pH of about 4.0 to about 9.0, preferably about 4.5 to about 8.0. The cultivation period varies depending upon the particular microorganism and nutrient medium used, and is generally in the range of about 10 to about 150 hours. The temperature range for carrying out the cultivation is conveniently from about 20 to about 45° C., preferably from 25 to 40° C.

The riboflavin glucosides thus accumulated consist of a mixture of those having one or more glucose moieties per molecule of riboflavin. If desired, the so-produced riboflavin glucosides can be easily concentrated to riboflavin monoglucoside, and this can be recovered, for example, by the following procedure: The culture broth containing riboflavin and riboflavin glucosides is first filtered or centrifuged to remove cells. Then the separated filtrate is treated with glucoamylase, whereby riboflavin glucosides are concentrated to riboflavin monoglucoside. About 1 unit of glucoamylase/mg riboflavin glucosides is usually sufficient for this purpose (one unit liberates 1.0 mg of glucose from starch in 3 minutes at pH 4.5 and 55° C.). The amount of enzyme employed depends on the incubation temperature, period and other reaction conditions, e.g. pH. If the enzyme concentration and/or temperature are low, a long incubation period is required. Two to three days incubation at 37° C. has been tried and showed good results. Considering these data, 0.001 to 100 units/mg, at 25 to 70° C. for 1 minute to 100 hours, preferably 0.1 to 10 units/mg at 30 to 60° C. for 3 minutes to 70 hours, are suitably employed. For further purification, if desired, the treated solution may be applied to an adsorbent resin. Regardless of whether riboflavin monoglucoside itself is to be obtained, the riboflavin glucoside accumulated in the fermentation can be isolated from the fermentation medium by standard techniques, preferably involving adsorbent resin and gel filtration resin for the separation of each component.

The invention now having been described in general terms, the following Figure and Examples are presented to illustrate the invention in more detail, without limiting it in any manner.

EXAMPLE 1

One loopful of *Bacillus subtilis* RB50::[pRF69]60::[pRF93]120Ade+ grown on an agar plate of Tryptose Blood Agar Base (TBAB, DIFCO Laboratories, Detroit, USA) medium containing 60 µg/ml of chloramphenicol and 120 µg/ml of tetracycline was inoculated into 8 ml of seed culture medium contained in a test tube.

The contents of the test tube were incubated at 37° C. for 2.75 hours using a tube shaker. The seed culture thus prepared (4 ml) was inoculated into a production medium made up to 40 ml after inoculation in a 500 ml Erlenmeyer flask with buffles. The composition of the seed culture and production medium was as follows.

|  | seed culture | production medium |
| --- | --- | --- |
| yeast extract | 20.0 g/l | 20.0 g/l |
| $KH_2PO_4$ | 7.5 | 7.5 |
| sodium glutamate | 5.0 | 5.0 |
| $(NH_4)_2SO_4$ | 5.0 | 5.0 |
| $MgCl_2.6H_2O$ | 1.5 | 1.5 |
| $MnSO_4.nH_2O$ | 0.05 | 0.05 |
| $CaCl_2.2H_2O$ | 1.0 | 1.0 |
| $FeCl_3.6H_2O$ | 0.025 | 0.025 |
|  | pH 6.7 before sterilization | |
| glucose | 13.3 g/l | — |
| maltose | 26.7 | — |
| soluble starch | — | 200 g/l |

(n in $MnSO_4.nH_2O$ signifies an integer 4 to 6 in view of the variable extent of hydration of the manganese sulphate).

The production medium was incubated at 37° C. and 240 rpm for 3 days. The broth was analyzed for the production level of riboflavin-related compounds by thin layer chromatography. One µl of the broth was spotted on a silica gel plate (Kieselgel 60F254, MERCK, Darmstadt, Germany) and developed by a solvent system consisting of acetone, n-butanol and water in a volume ratio of 5:4:1. At least three compounds other than riboflavin, designated component A, B and C and all yellow in colour, were detected. The Rf values for the components A, B, C and riboflavin were 0.27, 0.15, 0 (remaining at the spotted point after development) and 0.41, respectively. Accordingly, the component A is predominant. In direct comparison with flavin mononucleotide or flavin-adenin dinucleotide, it was demonstrated that none of the components corresponded to these nucleotides.

HPLC analysis of the culture broth was effected under the conditions described in FIG. 1. The retention time of the component A was 8.6 minutes, while that of riboflavin was 9.6 minutes. The TV-Vis. absorption spectra of the components A, B and C coincided well with that of riboflavin.

The total productivity of the components A, B and C measured by the UV absorption at 444 nm was 3.51 g/l based on riboflavin.

EXAMPLE 2

A culture broth obtained in a similar manner to Example 1 was treated with glucoamylase (EC 3.2.1.3) of *Aspergillis niger* (Sigma Chemical Co., Missouri, USA) in sodium acetate buffer (pH 4.5) at 55° C. for 2.5 hours. By thin layer chromatography analysis, the components A, B and C in the culture broth were observed to be centered at component A. Furthermore, a spot identical with authentic glucose was detected. Thus glucose was released from the components B and C by the treatment. The solution was then applied to a column packed with an adsorbent resin, Amberlite® XAD-7 (Rohm and Haas Co., Philadelphia, USA). Both the component A and riboflavin were adsorbed by the resin (glucose was not adsorbed) and eluted with a 1:1 aqueous acetone solution after washing with water. After concentration by evaporation to remove acetone, the eluate was freeze-dried. The resulting powder was dissolved in a small amount of sodium hydroxide solution and applied to a column packed with a gel filtration resin, Toyopearl HW-40F (TOYO SODA Mfg. Co. Ltd., Tokyo, Japan), to separate the component A and riboflavin. The eluted component A fraction was freeze-dried. The purity of the so-obtained powder was 97%.

The molecular weight of the component A was determined by a mass spectrometer to be m/z 539. This value corresponds to the molecular weight of riboflavin monoglucoside. The component A was then hydrolysed by 1N hydrochloric acid at 95° C. for 2.5 hours to investigate the possibility that a glucose moiety is attached to riboflavin. The hydrolysate was then spotted on a thin layer chromatographic plate together with authentic samples of riboflavin and glucose, and developed. As a result, it was established that riboflavin and glucose had been released from the component A. Furthermore, analysis of the 1H- and 13C-NMR spectra of the component A showed that the glucosidic bond consisted of an alpha-linkage at the 5'-position of riboflavin. From these results, the component A is concluded to be identical to 5'-D-riboflavin alpha-D-glucoside: 6,7-dimethyl-9-(5'-[α-D-glucopyranosyl]-D-ribityl)-isoalloxazine.

EXAMPLE 3

*Bacillus pumilus* RLX3, a yellow coloured riboflavin-producing mutant strain derived from *Bacillus pumilus* RC15 (FERM-BP No. 2834, JP Kokai No. 203982/1995 by two N-methyl-N'-nitro-N-nitrosoguanidine treatments, was cultivated in the same manner as described in Example 1, except that no antibiotics were added for this strain. As a result, 0.25 g/l of riboflavin glucoside (based on riboflavin measured by the UV absorption at 444 nm) was produced after 3 days of cultivation.

What is claimed is:

1. A process for producing a riboflavin glucoside, which comprises cultivating a microorganism having amylase activity and belonging to the genus Bacillus in an aqueous nutrient culture medium containing a starch under aerobic conditions, and recovering the riboflavin glucoside produced by the microorganism, wherein production of the riboflavin glucoside by the microorganism does not require exogenous riboflavin.

2. A process according to claim 1, wherein the microorganism is selected from the group consisting of *Bacillus brevis, Bacillus cereus, Bacillus circulans, Bacillus coagulans, Bacillus licheniformis, Bacillus megaterium, Bacillus pumilus* and *Bacillus subtilis*.

3. The process according to claim 2, wherein the microorganism is selected from the group consisting of *Bacillus brevis* IFO 15304, *Bacillus cereus* IFO 15305, *Bacillus circulans* IFO 13626, *Bacillus coagulans* IFO 12583, *Bacillus licheniformis* IFO 12200, *Bacillus megaterium* IFO 15308, *Bacillus pumilus* IFO 12092, *Bacillus subtilis* IFO 13719, *Bacillus subtilis* RB50::[pRF69]60Ade+ and *Bacillus subtilis* RB50::[pRF69]60[pRF93]120Ade+.

4. The process according to claim 3, wherein the microorganism is selected from the group consisting of *Bacillus brevis* IFO 15304, *Bacillus cereus* IFO 15305, *Bacillus circulans* IFO 13626, *Bacillus coagulants* IFO 12583, *Bacillus licheniformis* IFO 12200, *Bacillus megaterium* IFO 15308, *Bacillus pumilus* IFO 12092, and *Bacillus subtilis* IFO 13719.

5. The process according to claim 3, wherein the microorganism is selected from consisting of *Bacillus subtilis* RB50::[pRF69]60Ade+ and *Bacillus subtilis* RB50::[pRF69]60[pRF93]120Ade+.

6. The process according to claim 1, wherein the starch is present in the culture medium at a concentration of from about 25 g/l to about 400 g/l.

7. The process according to claim 6, wherein the starch is present in the culture medium at a concentration of from about 200 g/l to about 300 g/l.

8. The process according to claim 1, wherein the starch is selected from the group consisting of soluble starch, potato starch, corn starch and wheat starch.

9. The process according to claim 1, wherein the cultivation is carried out at a pH of about 4.0 to about 9.0.

10. The process according to claim 9, wherein the cultivation is carried out at a pH of about 4.5 to about 8.0.

11. The process according claim 1, wherein the cultivation is carried out at a temperature of from about 20 to about 45° C.

12. The process according to claim 11, wherein the cultivation is carried out at a temperature of from about 25 to about 40° C.

13. A process for producing riboflavin glucoside therefor according to claim 1 which comprises cultivating *Bacillus subtilis* RB50::[pRF69]60[pRF93]120Ade+.

14. A process for producing riboflavin glucoside therefor according to claim 1 which comprises cultivating *Bacillus subtilis* RB50::[pRF69]60Ade+.

* * * * *

UNITED STATES PATENT AND TRADEMARK OFFICE
CERTIFICATE OF CORRECTION

PATENT NO. : 6,190,888 B1
DATED : February 20, 2001
INVENTOR(S) : Tatsuo Hoshino et al.

It is certified that error appears in the above-identified patent and that said Letters Patent is hereby corrected as shown below:

<u>Title page,</u>
Under Item [75] Inventors, please change "Kamakura" to -- Kamakura-shi -- and "Yokohama" to -- Yokohama-shi --;

Throughout the patent, all instances of "Bacillus" should be italicized.

<u>Column 6,</u>
Line 27, after "from" please insert -- the group --;
Line 49, please delete "therefor;"
Line 52, please delete "therefor."

Signed and Sealed this

Eleventh Day of December, 2001

Attest:

Nicholas P. Godici

NICHOLAS P. GODICI
*Attesting Officer* *Acting Director of the United States Patent and Trademark Office*